United States Patent [19]
Hamilton et al.

[11] Patent Number: 5,968,957
[45] Date of Patent: Oct. 19, 1999

[54] METHOD OF USING NEUROTROPHIC SULFONAMIDE COMPOUNDS

[75] Inventors: Gregory S. Hamilton, Catonsville; Jia-He Li, Cockeysville; Joseph P. Steiner, Hampstead, all of Md.

[73] Assignee: GPI NIL Holdings, Inc., Wilmington, Del.

[21] Appl. No.: 09/028,517

[22] Filed: Feb. 23, 1998

Related U.S. Application Data

[62] Division of application No. 08/799,407, Feb. 12, 1997, Pat. No. 5,721,256.

[51] Int. Cl.$^6$ ........................ A61K 31/445; A61K 31/44; A61K 31/40
[52] U.S. Cl. ........................ 514/330; 514/317; 514/318; 514/343; 514/422; 514/423
[58] Field of Search ..................................... 514/330, 317, 514/318, 343, 422, 423

[56] References Cited

U.S. PATENT DOCUMENTS

| | | |
|---|---|---|
| 4,692,458 | 9/1987 | Ryan et al. . |
| 4,734,420 | 3/1988 | Ryan et al. . |
| 4,745,124 | 5/1988 | Ryan et al. . |
| 5,229,387 | 7/1993 | Clark et al. . |
| 5,585,397 | 12/1996 | Tung et al. . |
| 5,614,547 | 3/1997 | Hamilton et al. . |
| 5,696,135 | 12/1997 | Steiner et al. . |
| 5,721,256 | 2/1998 | Hamilton et al. . |
| 5,786,378 | 7/1998 | Hamilton et al. . |
| 5,795,908 | 8/1998 | Hamilton et al. . |
| 5,798,355 | 8/1998 | Steiner et al. . |
| 5,801,187 | 9/1998 | Li et al. . |
| 5,801,197 | 9/1998 | Steiner et al. . |

FOREIGN PATENT DOCUMENTS

| | | |
|---|---|---|
| WO92/21313 | 12/1992 | WIPO . |
| WO94/05639 | 3/1994 | WIPO . |
| WO95/24385 | 9/1995 | WIPO . |
| WO96/33184 | 10/1996 | WIPO . |
| WO 96/41609 | 12/1996 | WIPO . |

OTHER PUBLICATIONS

Holt et al., "Structure–Activity Studies of Synthetic FKBP Ligands as Peptidyl–Prolyl Isomerase Inhibitors," Bioorganic & Medicinal Chemistry Letters, vol. 4, No. 2, pp. 315–320, 1994.

Dumont, Francis J. et al., "The Immunosuppressive and Toxic Effects of FK–506 are Mechanistically Related: Pharmacology of a Novel Antagonist of FK–506 and Rapamycin," *J. Exp. Med.*, 1992, 176, 751–760.

Schreiber, Stuart L., "Chemistry and Biology of the Immunophilins and Their Immunosuppressive Ligands," *Science*, 1991, 251, 282–287.

*Primary Examiner*—William R. A. Jarvis
*Attorney, Agent, or Firm*—Nath & Associates; Gary M. Nath; Todd L. Juneau

[57] ABSTRACT

This invention relates to a method of using neurotrophic low molecular weight, small molecule piperidine and pyrrolidine sulfonamide compounds having an affinity for FKBP-type immunophilins, as inhibitors of the enzyme activity associated with immunophilin proteins, particularly peptidyl-prolyl isomerase, or rotamase, enzyme activity.

20 Claims, No Drawings

METHOD OF USING NEUROTROPHIC SULFONAMIDE COMPOUNDS

This application is a division of U.S. Ser. No. 08/799,407, filed Feb. 12, 1997, now U.S. Pat. No. 5,721,256.

BACKGROUND OF THE INVENTION

1. Field of Invention

This invention relates to a method of using neurotrophic low molecular weight, small molecule sulfonamide compounds having an affinity for FKBP-type immunophilins, as inhibitors of the enzyme activity associated with immunophilin proteins, particularly peptidyl-prolyl isomerase, or rotamase, enzyme activity.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., Science, 1990, vol. 250, pp. 556–559. Instead, immunosuppression appears to stem from the formulation of a complex of immunosuppressant drug and immunophilin. It has been shown that immunophilin-drug complexes interact with ternary protein targets as their mode of action. Schreiber et al., Cell, 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

Surprisingly, it has been found that certain low molecular weight, small peptidic sequences with a high affinity for FKBPs are potent rotamase inhibitors and exhibit excellent neurotrophic effects. Furthermore, these rotamase inhibitors are devoid of immunosuppressive activity. These findings suggest the use of rotamase inhibitors in treating various peripheral neuropathies and enhancing neuronal regrowth in the central nervous system (CNS). Studies have demonstrated that neurodegenerative disorders such as Alzheimer's disease, Parkinson's disease, and amyotrochic lateral sclerosis (ALS) may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF) It has thus been proposed to treat SDAT patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopo et al., J. Am. Soc. Nephrol., 1991, 1:162); neurological deficits, such as involuntary tremors, or non-specific cerebral angina, such as non-localized headaches (De Groen et al., N. Engl. J. Med., 1987, 317:861); and vascular hypertension with complications resulting therefrom (Kahan et al., N. Engl. J. Med., 1989, 321:1725).

To prevent the side effects associated with the use of the immunosuppressant compounds, the present invention provides a method of using a non-immunosuppressive compound containing low molecular weight, small molecule peptidic sequences to enhance neurite outgrowth, and to promote neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease), and amyotrophic lateral sclerosis.

SUMMARY OF THE INVENTION

The present invention relates to a method of using a neurotrophic low molecular weight, small molecule sulfonamide compound having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the neurotrophic compounds is that they do not exert any significant immunosuppressive activity.

Specifically, the present invention relates to a method of effecting a neuronal activity in an animal, comprising:

administering to the animal a neurotrophically effective amount of a compound of formula I:

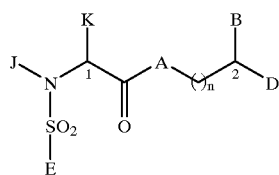

or a pharmaceutically acceptable salt thereof, wherein:
A is $CH_2$, oxygen, NH or N-(C1–C4 alkyl);
B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

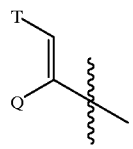

provided that both B and D are not hydrogen;
Q is hydrogen, (C1–C6)-straight or branched alkyl or (C1–C6)-straight or branched alkenyl;
T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;
Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, (C1–C6)-straight or branched alkyl, (C2–C6)-straight or branched alkenyl, O-(C1–C4)-straight or branched alkyl, O-(C2–C4)-straight or branched alkenyl, O-benzyl, O-phenyl, 1,2 -methylenedioxy, amino, carboxyl and phenyl;
E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)-alkyl or (C2–C4)-alkenyl)]-Ar or Ar;
J is hydrogen or C1 or C2 alkyl or benzyl; K is (C1–C4)-straight or branched alkyl, benzyl or cyclohexylmethyl; or wherein J and K may be taken together to form a 5–7 membered heterocyclic ring which may contain an oxygen, sulfur, SO or $SO_2$ substituent therein;

n is 0 to 3; and
the stereochemistry at carbon positions 1 and 2 are R or S.

The present invention also relates to a method of effecting a neuronal activity in an animal, comprising:
administering to the animal a neurotrophically effective amount of a compound of formula III:

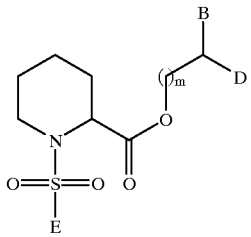

or a pharmaceutically acceptable salt thereof, wherein:
B and D are Independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

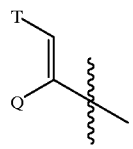

provided that both B and D are not hydrogen;
Q is hydrogen, (C1–C6)-straight or branched alkyl or (C1–C6)-straight or branched alkenyl;
T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;
Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, (C1–C6)-straight or branched alkyl, (C2–C6)-straight or branched alkenyl, O-(C1–C4)-straight or branched alkyl, O-(C2–C4)-straight or branched alkenyl, O-benzyl, O-phenyl, 1,2-methylenedioxy, amino, carboxyl and phenyl;
E is (C1–C6)-straight or branched alkyl, (C1–C6)-straight or branched alkenyl, (C5–C7)-cycloalkyl, (C5-C7)- cycloalkenyl substituted with (C1–C4)-straight or branched alkyl or (C1–C4)-straight or branched alkenyl, [(C2–C4)-alkyl or (C2–C4)-alkenyl)]-Ar or Ar; and m is 0 to 3.

The present invention further relates to a method of effecting a neuronal activity in an animal, comprising:

administering to the animal a neurotrophically effective amount of a compound of formula IV:

IV

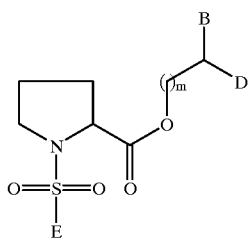

or a pharmaceutically acceptable salt thereof, wherein:

B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

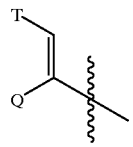

provided that both B and D are not hydrogen;

Q is hydrogen, (C1–C6)-straight or branched alkyl or (C1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, (C1–C6)-straight or branched alkyl, (C2–C6)-straight or branched alkenyl, O-(C1–C4)-straight or branched alkyl, O-(C2–C4)-straight or branched alkenyl, O-benzyl, O-phenyl, 1,2-methylenedioxy, amino, carboxyl and phenyl;

E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)-alkyl or (C2–C4)-alkenyl)]-Ar or Ar; and m is 0 to 3.

DETAILED DESCRIPTION OF THE INVENTION

Definitions

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Halo" means fluoro, chloro, bromo, or iodo, unless otherwise indicated.

"Pharmaceutically acceptable salt" refers to salts of the subject compounds which possess the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

"Phenyl" includes all possible isomeric phenyl radicals, optionally monosubstituted or multi-substituted with substituents selected from the group consisting of alkyl, alkoxy, hydroxy, halo, and haloalkyl.

"Treatment" covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; and (iii) relieving the disease and/or condition, i.e., causing regression of the disease and/or condition.

The inventors have discovered that certain low molecular weight, small molecule sulfonamide compounds have an affinity for FKBP-type immunophilins, particularly FKBP12. When the sulfonamide compounds are bound to an FKBP-type immunophilin, they have been found to inhibit the prolyl-peptidyl cis-trans isomerase activity, or rotamase, activity of the binding protein and unexpectedly stimulate neurite growth. This activity is useful in the stimulation of damaged neurons, the promotion of neuronal regeneration, the prevention of neurodegeneration, and the treatment of several neurological disorders known to be associated with neuronal degeneration and peripheral neuropathies.

For the foregoing reasons, the present invention relates to a method of effecting a neuronal activity in an animal, comprising:

administering to the animal a neurotrophically effective amount of a compound of formula I:

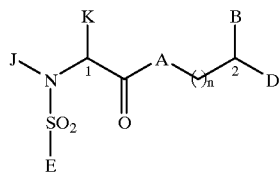

I or a pharmaceutically acceptable salt thereof, wherein:

A is $CH_2$, oxygen, NH or N-(C1–C4 alkyl);

B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

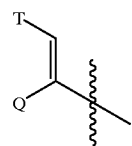

provided that both B and D are not hydrogen;

Q is hydrogen, (C1–C6)-straight or branched alkyl or (C1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, (C1–C6)-straight or branched alkyl, (C2–C6)-straight or branched alkenyl, O-(C1–C4)-straight or branched alkyl, O-(C2–C4)-straight or branched alkenyl, O-benzyl, O-phenyl, 1,2-methylenedioxy, amino, carboxyl and phenyl;

E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)-alkyl or (C2–C4)-alkenyl)]-Ar or Ar;

J is hydrogen or C1 or C2 alkyl or benzyl; K is (C1–C4)-straight or branched alkyl, benzyl or cyclohexylmethyl; or wherein J and K may be taken together to form a 5–7 membered heterocyclic ring which may contain an oxygen, sulfur, SO or $SO_2$ substituent therein;

n is 0 to 3; and the stereochemistry at carbon positions 1 and 2 are R or S.

In a preferred embodiment, J and K are taken together and the compound is represented by formula II:

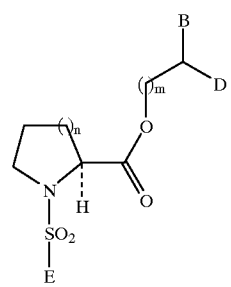

II wherein n is 1 or 2 and m is 0 or 1.

In a more preferred embodiment, B is selected from the group consisting of hydrogen, benzyl, 2-phenylethyl and 3-phenylpropyl; D is selected from the group consisting of phenyl, 3-phenylpropyl, 3-phenoxyphenyl and 4-phenoxyphenyl; and E is selected from the group consisting of phenyl, 4-methylphenyl, 4-methoxyphenyl, 2-thienyl, 2,4,6-triisopropylphenyl, 4-fluorophenyl, 3-methoxyphenyl, 2-methoxyphenyl, 3,5-dimethoxyphenyl, 3,4,5-trimethoxyphenyl, methyl, 1-naphthyl, 8-quinolyl, 1-(5-N, N-dimethylamino)-naphthyl, 4-iodophenyl, 2,4,6-trimethylphenyl, benzyl, 4-nitrophenyl, 2-nitrophenyl, 4-chlorophenyl and E-styrenyl.

The present invention also relates to a method of effecting a neuronal activity in an animal, comprising:

administering to the animal a neurotrophically effective amount of a compound of formula III:

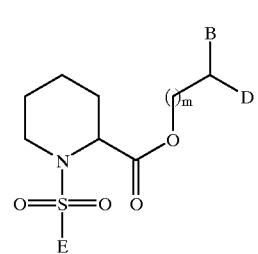

III or a pharmaceutically acceptable salt thereof, wherein:

B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and SO$_2$ in chemically reasonable substitution patterns, or

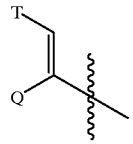

provided that both B and D are not hydrogen;

Q is hydrogen, (C1–C6)-straight or branched alkyl or (C1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, (C1–C6)-straight or branched alkyl, (C2–C6)-straight or branched alkenyl, O-(C1–C4)-straight or branched alkyl, O-(C2–C4)-straight or branched alkenyl, O-benzyl, O-phenyl, 1,2-methylenedioxy, amino, carboxyl and phenyl;

E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)-alkyl or (C2–C4)-alkenyl)]-Ar or Ar; and m is 0 to 3.

The present invention further relates to a method of effecting a neuronal activity in an animal, comprising:

administering to the animal a neurotrophically effective amount of a compound of formula IV:

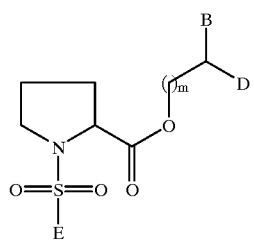

IV or a pharmaceutically acceptable salt thereof, wherein:

B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the CH$_2$ groups of the alkyl or alkenyl chains may contain 1–2 heteroatoms selected from the group consisting of oxygen, sulfur, SO and SO$_2$ in chemically reasonable substitution patterns, or

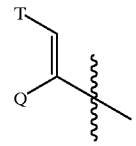

provided that both B and D are not hydrogen;

Q is hydrogen, (C1–C6)-straight or branched alkyl or (C1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, (C1–C6)-straight or branched alkyl, (C2–C6)-straight or branched alkenyl, O-(C1–C4)-straight or branched alkyl, O-(C2–C4)-straight or branched alkenyl, O-benzyl, O-phenyl, 1,2-methylenedioxy, amino, carboxyl and phenyl;

E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)-alkyl or (C2–C4)-alkenyl)]-Ar or Ar; and m is 0 to 3.

The neuronal activity that is effected by the methods of the present invention may be selected from the group consisting of: stimulation of damaged neurons, promotion of neuronal regeneration, prevention of neurodegeneration and treatment of a neurological disorder.

Examples of a neurological disorder that is treatable by the methods of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; and Parkinson's disease.

The methods of the present invention are particularly useful for treating a neurological disorder selected from the group consisting of: peripheral neuropathy caused by physical injury or disease state, physical damage to the brain, physical damage to the spinal cord, stroke associated with brain damage, and a neurological disorder relating to neurodegeneration. Examples on a neurological disorder relating to neurodegeneration include Alzheimer's Disease, Parkinson's Disease, and amyotrophic lateral sclerosis.

In the methods of the present invention, the neurotrophic compound may be administered orally, parenterally, by inhalation spray, topically, rectally, nasally, buccally, vaginally or via an implanted reservoir in dosage formulations containing conventional non-toxic parmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the neurotrophic compounds should readily penetrate the blood-brain barrier when peripherally administered. Compounds which cannot penetrate the blood-brain barrier can be effectively administered by an intraventricular route.

The neurotrophic compounds may also be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, the neurotrophic compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The neurotrophic compounds may further be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

Moreover, the neurotrophic compounds may be administered topically, especially when the conditions addressed for treatment involve areas or organs readily accessible by topical application, including neurological disorders of the eye, the skin, or the lower intestinal tract. Suitable topical formulations can be readily prepared for each of these areas.

For topical application to the eye, or ophthalmic use, the compounds can be formulated as micronized suspensions in isotonic, pH adjusted sterile saline, or, preferably, as a solution in isotonic, pH adjusted sterile saline, either with or without a preservative such as benzylalkonium chloride. Alternatively, the compounds may be formulated into ointments, such as petrolatum, for ophthalmic use.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in a rectal suppository formulations (see above) or in suitable enema formulations.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex, and diet of the patient; the time of administration; the rate of excretion; drug combination; the severity of the particular disease being treated; and the form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

EXAMPLES

The following examples are illustrative of the present invention and are not intended to be limitations thereon. Unless otherwise specified, all percentages are based on 100% by weight of the final compound.

The compounds used in the methods of the present invention may be readily prepared by standard techniques of organic chemistry, utilizing the general synthetic pathway depicted below. As described by Scheme I, amino acids 1 protected by suitable blocking groups P on the amino acid nitrogen may be reacted with alcohols ROH to generate esters 2. After removal of the protecting group, the free amine 3 may be reacted with various sulfonyl chlorides 4 to provide final products 5 in good to excellent yield.

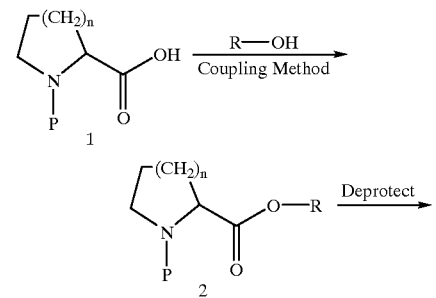

Scheme I

-continued

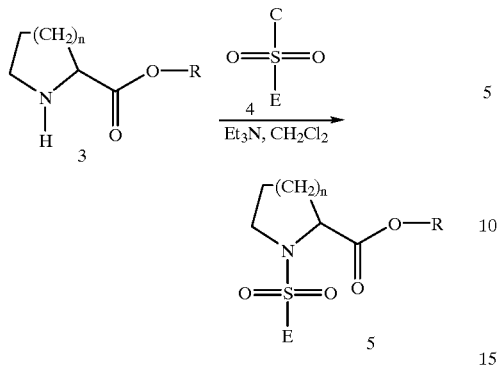

In the compounds depicted above in Scheme I, E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)-alkyl or (C2–C4)-alkenyl)]-Ar or Ar; and R is $(CH_2)_n$ CHBD, wherein B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

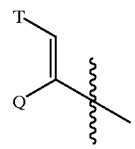

provided that both B and D are not hydrogen.

Example 1

Synthesis of 3-(3-Pyridyl)-1-propyl(2S)-N-(α-toluenesulfonyl)pyrrolidine-2-carboxylate (1)

3-(3-Pyridyl)-1-propyl N-(tert-butyloxy-carbonyl)pyrrolidine-2-carboxylate

A mixture of N-(tert-butyloxycarbonyl)-(S)-proline (6.0 g; 28 mmol); 3-(3-pyridyl)-1-propanol (5.80 g; 41.8 mmol), dicyclohexylcarbodiimide (9.20 g; 44.48 mmol), camphorsulfonic acid (21.60 g; 9.26 mmol) and 4-dimethylaminopyridine (1.12 g; 9.26 mmol) in dry methylene chloride (200 mL) was stirred overnight. The reaction mixture was filtered through Celite, concentrated, and purified on a silica gel column eluting with 40% ethyl acetate in hexane to obtain 5.0 g of the product as a clear oil (53%), $^1$H NMR (300 MHz, $CDCl_3$): δ 1.42 (s, 9H); 1.43–1.95 (m, 6H); 2.68 (m, 2H); 3.46–3.52 (m, 2H); 4.11–4.22 (m, 2H); 4.33 (m, 1H); 7.17–7.24 (m, 1H); 7.47 (m, 1H); 8.43 (s, 2H).

3-(3-Pyridyl)-1-propyl pyrrolidine-2-carboxylate

A solution of 3-(3-pyridyl)-1-propyl N-(tert-butyloxycarbonyl)pyrrolidine-2-carboxylate (3.0 g; 8.9 mmol) in methylene chloride (40 mL) and trifluoroacetic acid (8 mL) was stirred at room temperature for three hours. Saturated potassium carbonate was added until the pH was basic, and the reaction mixture was extracted with methylene chloride (3×). The combined organic extracts were dried and concentrated to yield 1.60 g (77%) of the free amine as a thick oil, $^1$H NMR (300 MHz, $CDCl_3$): δ 1.71–2.09 (m, 6H); 2.63 (m, 2H); 2.86 (m, 1H); 2.94 (m, 1H); 3.71 (m, 1H); 4.11 (m, 2H); 7.18 (m, 1H); 7.45 (m, 1H); 8.41 (m, 2H).

3-(3-Pyridyl)-1-propyl (2S)-N-(α-toluenesulfonyl)pyrrolidine-2-carboxylate (1)

A solution of 3-(3-Pyridyl)-1-propyl pyrrolidine-2-carboxylate (200 mg; 0.9 mmol) and α-toluenesulfonyl chloride (160 mg; 0.9 mmol) in methylene chloride (20 mL) was treated with triethylamine (90 mg; 0.9 mmol) and stirred for 2 hours at room temperature. The reaction mixture was filtered to remove solids and applied directly to a silica gel column, eluting with 50% ethyl acetate in hexane, to obtain 150 mg (43%) of compound 1 (Table I) as a clear oil, $^1$H NMR (300 MHz, $CDCl_3$): δ 1.81–1.85 (m, 2H); 1.95–2.02 (m, 3H); 2.10–2.25 (m, 1H); 2.69–2.74 (t, 2H); 2.85–2.97 (m, 1H); 3.24–3.27 (m, 1H); 4.16–4.20 (m, 2H); 4.29 (d, 1H); 4.34 (m, 1H); 4.45 (d, 1H); 7.20–7.25 (m, 1H); 7.35 (m, 3H); 7.49–7.52 (m, 3H); 8.46 (s, 2H). Anal. Calcd. for $C_{20}H_{24}N_2O_3S$: C, 61.83; H, 6.23; N, 7.21. Found: C, 61.59; H, 6.24; N, 7.17.

Example 2

Synthesis of 4-Phenyl-1-butyl 1-(α-tolylsulfonyl)-2-pipecolinate (2)

Methyl 1-(α-tolylsulfonyl)-2-pipecolinate

To a solution of methyl pipecolinate hydrochloride (1.79 g; 10 mmol) and triethylamine (1.01 g; 10 mmol) in dry methylene chloride (20 mL) was added α-toluenesulfonyl chloride (1.9 g; 10 mmol). The resulting mixture was stirred at room temperature overnight and then concentrated in vacua. The crude residue was purified on a silica gel column, eluting with ethyl acetate, to provide 2.20 g (74%) of the product was an oil which solidified upon standing, $^1$H NMR ($CDCl_3$, 300 MHz): δ 1.26–1.71 (m, 5H); 2.15 (d, 1H, J=14.4); 3.17 (dt, 1H); 3.45 (d, 1H, J=12.6); 3.78 (s, 3H); 4.28 (s, 2H); 4.58 (m, 1H); 7.26–7.48 (m, 5H).

N-(α-tolylsulfonyl)-2-pipecolic acid

Methyl 1-(α-tolylsulfonyl)-2-pipecolinate (2.0 g; 6.72 mmol) was dissolved in ethanol (25 mL) and treated with 20 mL of 1N lithium hydroxide. The mixture was stirred for 2 hours at room temperature, and then diluted with ethyl acetate (200 mL) and made acidic (pH 2) with 1N HCL. The organic layer was washed with brine, dried over magnesium sulfate, and concentrated to obtain 1.90 g (100%) of the acid as a white solid.

4-Phenyl-1-butyl 1-(α-tolylsulfonyl)-2-pipecolinate (2)

A solution of N-(α-tolylsulfonyl)-2-pipecolic acid (400 mg; 1.41 mmol), dicyclohexylcarbodiimide (312 mg; 1.5 mmol), dimethylaminopyridine (7 mg) and 4-phenyl-1-butanol (240 mg; 1.60 mmol) in 100 mL of methylene chloride was stirred overnight at room temperature. The mixture was filtered through Celite, concentrated, and purified on a silica gel column, eluting with 25% ethyl acetate in hexane, to obtain 380 mg (48%) of compound 2 (Table I)

as a clear oil, $^1$H NMR (CDCl$_3$, 300 MHz): δ 1.10–1.69 (m, 5H); 1.70 (tt, 4H, J=6.1, 6.6); 2.15 (m, 1H); 2.66 (t, 2H, J=6.6); 3.16 (m, 1H); 3.45 (m, 1H); 4.19 (t, 2H, J=6.1); 4.28 (s, 2H); 4.58 (m, 1H); 7.18–7.47 (m, 10H). Anal. Calcd. for C$_{23}$H$_{29}$NO$_4$S: C, 66.48; H, 7.03; N, 3.37. Found: C, 66.34; H, 7.06; N, 3.41.

Example 3

Synthesis of 1,5-Diphenyl-3-pentyl (N-(α-toluenesulfonyl)pipecolate (3)

3-Phenyl-1-propanal

Oxalyl chloride (2.90 g; 2.29 mmol) in methylene chloride (50 mL), cooled to −78° C., was treated with dimethylsulfoxide (3.4 mL) in 10 mL of methylene chloride. After stirring for 5 minutes, 3-phenyl-1-propanol (2.72 g; 20 mmol) in 20 mL of methylene chloride was added, and the resulting mixture was stirred at −78° C. for 15 minutes, treated with 14 mL of triethylamine, stirred an additional 15 minutes, and poured into 100 mL of water. The layers were separated, the organic phase was dried and concentrated, and the crude residue was purified on a silica gel column, eluting with 10% ethyl acetate in hexane, to obtain 1.27 g (47%) of the aldehyde as a clear oil, $^1$H NMR (300 MHz, CDCl$_3$): δ 2.80 (m, 2H); 2.98 (m, 2H); 7.27 (m, 5H); 9.81 (s, 1H).

1,5-Diphenyl-3-pentanol

A solution of 2-(bromoethyl)benzene (1.73 g; 9.33 mmol) in diethylether (10 mL) was added to a stirred slurry of magnesium turnings (250 mg; 10.18 mmol) in 5 mL of ether. The reaction was initiated with a heat gun, and after the addition was complete the mixture was heated on an oil bath for 30 minutes. 3-Phenyl-1-propanal (1.25 g; 9.33 mmol) was added in 10 mL of ether, and reflux was continued for 1 hour. The reaction was cooled and quenched with saturated ammonium chloride, extracted into 2x ethyl acetate, and the combined organic portions were dried and concentrated. Chromatographic purification on a silica gel column (10% ethyl acetate in hexane) delivered 1.42 g (63%) of the diphenyl alcohol, $^1$H NMR (300 MHz, CDCl$_3$): δ 1.84 (m, 4H); 2.61–2.76 (m,4H); 3.65 (m, 1H); 7.19–7.29 (m, 10H).

1,5-Diphenyl-3-pentyl N-(α-toluenesulfonyl)-pipecolate (3)

A mixture of N-(α-tolylsulfonyl)-2-pipecolic acid (380 mg; 1.34 mmol), 1,5-diphenyl-3-pentanol (485 mg; 2.01 mmol), dicyclohexylcarbodiimide (445 mg; 2.15 mmol), camphorsulfonic acid (105 mg; 0.45 mmol) and dimethylaminopyridine (55 mg; 0.45 mmol) in 20 mL of methylene chloride was stirred overnight at room temperature. The mixture was filtered through Celite, concentrated, and purified on a silica gel column, eluting with 15% ethyl acetate in hexane, to obtain 270 mg (40%) of compound 3 (Table I) as a clear oil, $^1$H NMR (CDCl$_3$, 300 MHz): δ 0.80 (m, 4H); 1.23–1.97 (m, 5H) 2.15 (d, 1H); 2.61–2.69 (m, 4H); 3.23 (m, 1H); 3.44 (dm, 1H); 4.27 (s, 2H); 4.53 (d, 1H, J=4.5); 5.06 (m, 1H); 7.16–7.34 (m, 15H). Anal. calcd. for C$_{30}$H$_{35}$NO$_4$S: C, 71.26; H, 6.98; N, 2.77. Found: C, 72.82; H, 7.17; N, 2.53.

As discussed above, the sufonamide compounds used in the methods of the present invention have an affinity for the FKBP binding protein, particularly FKBP12. The inhibition of the prolyl peptidyl cis-trans isomerase activity of FKBP may be measured as an indicator of this affinity.

Ki Test Procedure

Inhibition of the peptidyl-prolyl isomerase (rotamase) activity of the inventive compounds can be evaluated by known methods described in the literature (Harding, et al., *Nature*, 1989, 341:758–760; Holt et al. *J. Am. Chem. Soc.*, 115:9923–9938). These values are obtained as apparent Ki's and are presented in Table I. The cis-trans isomerization of an alanine-proline bond in a model substrate, N-succinyl-Ala-Ala-Pro-Phe-p-nitroanilide, is monitored spectrophotometrically in a chymotropsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Ki values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table I under the column "Ki".

The neurotrophic effects of the compounds of the present invention can be demonstrated in cellular biological experiments in vitro, as described below.

Chick Dorsal Root Ganglion

Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% CO$_2$. Twenty-four hours later, the DRGs were treated with various immunophilin ligands. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The data for these experiments for representative compounds are presented in the "ED50" column of Table I.

TABLE I

In Vitro Activity of Example Compounds

| Compound | Ki, nM | ED50, nM |
|---|---|---|
| 4-phenyl-1-butyl-(α-toluenesulfonyl) pipecolate (2) | 34 | 0.031 |
| 1,5-diphenyl-3-pentyl-N-(α-toluenesulfonyl)-pipecolate (3) | 107 | 0.133 |
| 1,7-diphenyl-4-heptyl-N-(para-toluenesulfonyl)-pipecolate | 332 | 1.0 |
| 3-(3-pyridyl)-1-propyl-(2S)-N-(α-toluenesulfonyl)-pyrrolidine-2-carboxylate (1) | 72 | 0.002 |

TABLE I-continued

In Vitro Activity of Example Compounds

| Compound | Ki,nM | ED50,nM |
|---|---|---|
| 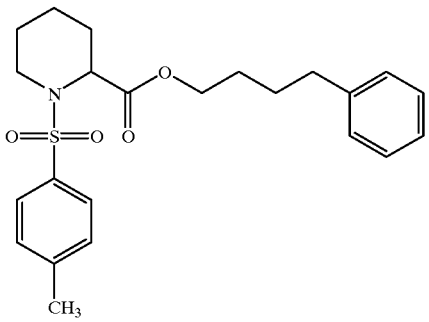<br>4-phenyl-1-butyl-N-(para-toluenesulfonyl)-pipecolate | 504 | — |
| 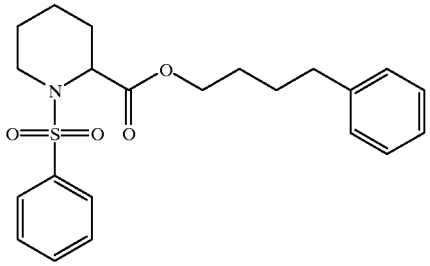<br>4-phenyl-1-butyl-N-(benzenesulfonyl)pipecolate | 470 | — |

MPTP Model of Parkinson's Disease

The remarkable neurotrophic and neuroregenerative effects of the present inventive compounds were further demonstrated in an animal model of neurodegenerative disease. MPTP lesioning of dopaminergic neurons in mice was used as an animal model of Parkinson's Disease. Four week old male CD1 white mice were dosed i.p. with 30 mg/kg of MPTP for 5 days. Test compounds (4 mg/kg), or vehicle, were administered s.c. along with the MPTP for 5 days, as well as for an additional 5 days following cessation of MPTP treatment. At 18 days following MPTP treatment, the animals were sacrificed and the striata were dissected and perfusion-fixed. Immunostaining was performed on saggital and coronal brain sections using anti-tyrosine hydroxylase 1 g quantitate survival and recovery of dopaminergic neurons. In animals treated with MPTP and vehicle, a substantial loss of functional dopaminergic terminals was observed as compared to non-lesioned animals. Lesioned animals receiving test compounds showed a significant recovery of TH-stained dopaminergic neurons. Table II cresents quantitation for the recovery of TH-positive dopaminergic neurons in the striatum of animals receiving compounds 1, 2, 5 and 6 in this model.

TABLE II

In Vivo Activity of Selected Example Compounds

| Compound | % Rescue, TH Immunostaining at 4 mg/kg, s.c. |
|---|---|
| 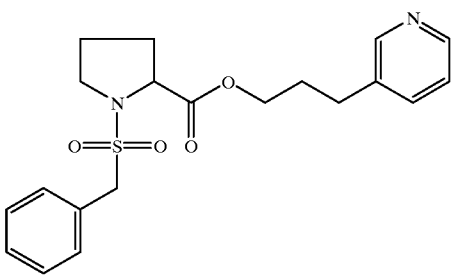 | 44.31 |

TABLE II-continued

In Vivo Activity of Selected Example Compounds

| Compound | % Rescue, TH Immunostaining at 4 mg/kg, s.c. |
|---|---|
| 3-(3-pyridyl)-1-propyl-(2S)-N-(α-toluenesulfonyl)-pyrrolidine-2-carboxylate (1) 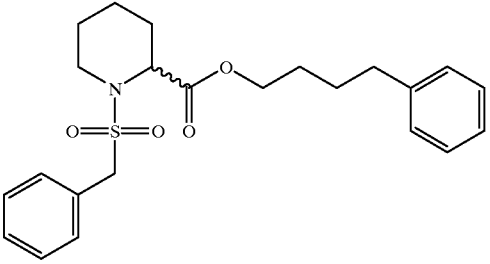 | 38.00 |
| 4-phenyl-1-butyl-N-(α-toluenesulfonyl)pipecolate (2) 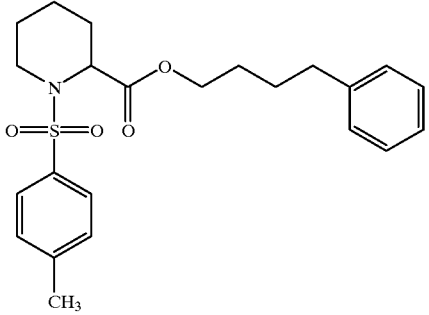 | 44.16 |
| 4-phenyl-1-butyl-N-(para-toluenesulfonyl)-pipecolate 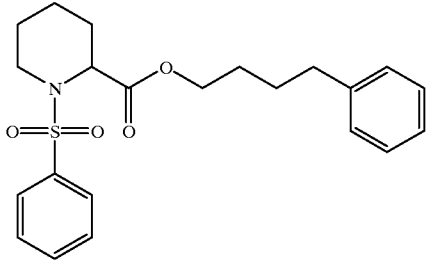 | 29.22 |
| 4-phenyl-1-butyl-N-(benzenesulfonyl)pipecolate | |

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of effecting a neuronal activity in an animal in need thereof, comprising:

administering to the animal a neurotrophically effective amount of a compound of formula I:

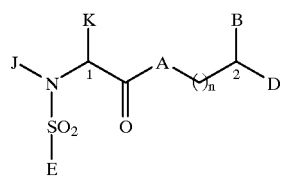

or a pharmaceutically acceptable salt thereof, wherein:

A is $CH_2$, oxygen, NH or N-$(C_1-C_4)$alkyl;

B and D are independently Ar, (C₁–C₆) straight or branched alkyl, (C₂–C₆) straight or branched alkenyl, (C₁–C₆) straight or branched alkyl or alkenyl that is substituted with a (C₅–C₇)cycloalkyl, (C₁–C₆) straight or branched alkyl or alkenyl that is substituted with a (C₅–C₇)cycloalkenyl, Ar substituted (C₁–C₆) straight or branched alkyl or alkenyl, wherein, in each case, one or two of the CH₂ of the alkyl or alkenyl chains may contain 1–2 heteroatoms selected from the group consisting of oxygen, sulfur, SO, and SO₂ in chemically reasonable substitution patterns, or

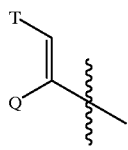

Q is hydrogen, (C1–C6)-straight or branched alkyl or (C-1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-naphthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar contains one to three substituents which are independently selected from the group consisting of hydrogen, halo, hydroxyl, nitro, trifluoromethyl, trifluoromethoxy, (C₁–C₆) straight or branched alkyl, (C₂–C₆) straight or branched alkenyl, O-(C₁–C₄) straight or branched alkyl, O-(C2–C4) straight or branched alkenyl, O-benzyl, O-phenyl, 1,2-methylenedioxy, amino, carboxyl, and phenyl;

E is (C₁–C₆) straight or branched alkyl, (C₂–C₆) straight or branched alkenyl, (C₅–C₇)cycloalkyl, (C₅–C₇) cycloalkenyl substituted with (C₁–C₄) straight or branched alkyl or (C₂–C₄) straight or branched alkenyl, [(C₂–C₄)alkyl or (C₂–C₄)alkenyl]-Ar, or Ar;

J and K are taken together to form a pyrrolidine or a piperidine ring;

n is 0 to 3; and the stereochemistry at carbon positions 1 and 2 are R or S.

2. The method of claim 1, wherein the neuronal activity is selected from the group consisting of stimulation of damaged neurons, promotion of neuronal regeneration, prevention or neurodegeneration and treatment of neurological disorder.

3. The method of claim 2, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

4. The method of claim 3, wherein the neurological disorder relating to neurodegeneration is selected from the group consisting of Alzheimer's Disease, Parkinson's Disease, and amyotrophic lateral sclerosis.

5. The method of claim 1, wherein the compound is represented by formula II:

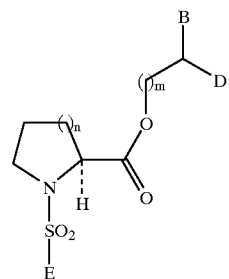

wherein n is 1 or 2 and m is 0 or 1.

6. The method of claim 5, wherein the neuronal activity is selected from the group consisting of stimulation of damaged neurons, promotion of neuronal regeneration, prevention of neurodegeneration and treatment of neurological disorder.

7. The method of claim 6, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

8. The method of claim 7, wherein the neurological disorder relating to neurodegeneration is selected from the group consisting of Alzheimer's Disease, Parkinson's Disease, and amyotrophic lateral sclerosis.

9. The method of claim 5, wherein:

B is selected from the group consisting of benzyl, 2-phenylethyl and 3-phenylpropyl;

D is selected from the group consisting of phenyl, 3-phenylpropyl, 3-phenoxyphenyl and 4-phenoxyphenyl; and E is selected from the group consisting of phenyl, 4-methylphenyl, 4-methoxyphenyl, 2-thienyl, 2,4,6-triisopropylphenyl, 4-fluorophenyl, 3-methoxyphenyl, 2-methoxyphenyl, 3,5-dimethoxyphenyl, 3,4,5-trimethoxyphenyl, methyl, 1-naphthyl, 8-quinolyl, 1-(5-N,N-dimethylamino)-naphthyl, 4-iodophenyl, 2,4,6-trimethylphenyl, benzyl, 4-nitrophenyl, 2-nitrophenyl, 4-chlorophenyl and E-styrenyl.

10. The method of claim 9, wherein the neuronal activity is selected from the group consisting of stimulation of damaged neurons, promotion of neuronal regeneration, prevention of neurodegeneration and treatment of neurological disorder.

11. The method of claim 10, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

12. The method of claim 11, wherein the neurological disorder relating to neurodegeneration is selected from the group consisting or Alzheimer's Disease, Parkinson's Disease, and amyotrophic lateral sclerosis.

13. A method of effecting a neuronal activity in an animal in need thereof, comprising:

administering to the animal a neurotrophically effective amount of a compound of formula III:

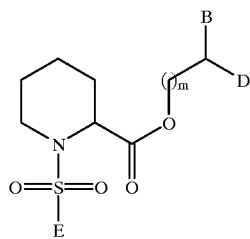

or a pharmaceutically acceptable salt thereof, wherein:

A is $CH_2$, oxygen, NH or N-$(C_1-C_4)$alkyl;

B and D are independently Ar, $(C_1-C_6)$ straight or branched alkyl, $(C_2-C_6)$ straight or branched alkenyl, $(C_1-C_6)$ straight or branched alkyl or alkenyl that is substituted with a $(C_5-C_7)$cycloalkyl, $(C_1-C_6)$ straight or branched alkyl or alkenyl that is substituted with a $(C_5-C_7)$cycloalkenyl, Ar substituted $(C_1-C_6)$ straight or branched alkyl or alkenyl, wherein, in each case, one or two of the $CH_2$ of the alkyl or alkenyl chains may contain 1–2 heteroatoms selected from the group consisting of oxygen, sulfur, SO, and $SO_2$ in chemically reasonable substitution patterns, or

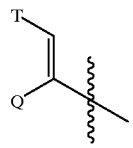

Q is hydrogen, (C1–C6)-straight or branched alkyl or (C1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-naphthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar contains one to three substituents which are independently selected from the group consisting of hydrogen, halo, hydroxyl, nitro, trifluoromethyl, trifluoromethoxy, (C1–C6) straight or branched alkyl, $(C_2-C_6)$ straight or branched alkenyl, O-$(C_1-C_4)$ straight or branched alkyl, O-$(C_2-C_4)$ straight or branched alkenyl, O-benzyl, O-phenyl, 1,2-methylenedioxy, amino, carboxyl, and phenyl;

E is $(C0-C_6)$ straight or branched alkyl, $(C_2-C_6)$ straight or branched alkenyl, $(C_5-C_7)$cycloalkyl, $(C_5-C_7)$ cycloalkenyl substituted with $(C_1-C_4)$ straight or branched alkyl or $(C_2-C_4)$ straight or branched alkenyl, [$(C_2-C_4)$alkyl or $(C_2-C_4)$alkenyl]-Ar, or Ar; and m is 0 to 3.

14. The method of claim 13, wherein the neuronal activity is selected from the group consisting of stimulation of damaged neurons, promotion of neuronal regeneration, prevention of neurodegeneration and treatment of neurological disorder.

15. The method of claim 14, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

16. The method of claim 15, wherein the neurological disorder relating to neurodegeneration is selected from the group consisting of Alzheimer's Disease, Parkinson's Disease, and amyotrophic lateral sclerosis.

17. A method of effecting a neuronal activity in an animal in need thereof, comprising:

administering to the animal a neurotrophically effective amount of a compound of formula IV:

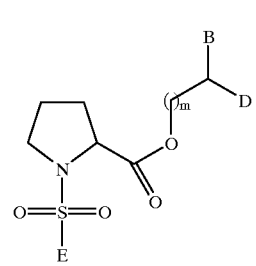

or a pharmaceutically acceptable salt thereof, wherein:

A is $CH_2$, oxygen, NH or N-$(C_1-C_4)$alkyl;

B and D are independently Ar, $(C_1-C_6)$ straight or branched alkyl, $(C_2-C_6)$ straight or branched alkenyl, $(C_1-C_6)$ straight or branched alkyl or alkenyl that is substituted with a $(C_5-C_7)$cycloalkyl, $(C_1-C_6)$ straight or branched alkyl or alkenyl that is substituted with a $(C_5-C_7)$cycloalkenyl, Ar substituted $(C_1-C_6)$ straight or branched alkyl or alkenyl, wherein, in each case, one or two of the $CH_2$ of the alkyl or alkenyl chains may contain 1–2 heteroatoms selected from the group consisting of oxygen, sulfur, SO, and $SO_2$ in chemically reasonable substitution patterns, or

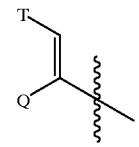

Q is hydrogen, (C1–C6)-straight or branched alkyl or (C1–C6)-straight or branched alkenyl;

T is Ar or substituted 5–7 membered cycloalkyl with substituents at positions 3 and 4 which are independently selected from the group consisting of hydrogen, hydroxyl, O-(C1–C4)-alkyl, O-(C1–C4)-alkenyl and carbonyl;

Ar is selected from the group consisting of phenyl, 1-naphthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar contains one to three substituents which are independently selected from the group consisting of hydrogen, halo, hydroxyl, nitro, trifluoromethyl, trifluoromethoxy, $(C_1-C_6)$ straight or branched alkyl, $(C_2-C_6)$ straight or branched alkenyl, O-$(C_1-C_4)$ straight or branched alkyl, O-$(C_2-C_4)$ straight or branched alkenyl, O-benzyl, O-phenyl, 1,2-methylenedioxy, amino, carboxyl, and phenyl;

E is $(C_1-C_6)$ straight or branched alkyl, $(C_2-C_6)$ straight or branched alkenyl, $(C_5-C_7)$cycloalkyl, $(C_5-C_7)$ cycloalkenyl substituted with $(C_1-C_4)$ straight or branched alkyl or $(C_2-C_4)$ straight or branched alkenyl, $[(C_2-C_4)$alkyl or $(C_2-C_4)$alkenyl]-Ar, or Ar; and m is 0 to 3.

18. The method of claim 17, wherein the neuronal activity is selected from the group consisting of stimulation of damaged neurons, promotion of neuronal regeneration, prevention or neurodegeneration and treatment of neurological disorder.

19. The method of claim 18, wherein the neurological disorder is selected from the group consisting of peripheral neuropathy caused by physical injury or disease state, physical damage to the brain, physical damage to the spinal cord, stroke associated with brain damage, and neurological disorder relating to neurodegeneration.

20. The method of claim 19, wherein the neurological disorder relating to neurodegeneration is selected from the group consisting of Alzheimer's Disease, Parkinson's Disease, and amyotrophic lateral sclerosis.

* * * * *

UNITED STATES PATENT AND TRADEMARK OFFICE
CERTIFICATE OF CORRECTION

PATENT NO. : 5,968,957
DATED : October 19, 1999
INVENTOR(S) : Gregory S. HAMILTON et al.

It is certified that error appears in the above-indentified patent and that said Letters Patent is hereby corrected as shown below:

Column 4, line 22, after "B and D are" and before "Ar, hydrogen (C1-C6)-", please replace "Independently" with --independently--.

Column 14, line 40, before ". The crude residue was purified", please replace "vacua" with --vacuo--.

Column 15, line 63, before "binding protein," please replace "FKBP" with --FK506--.

Column 16, line 11, after "in a" and before "-coupled assay,", please replace "chymotropsin" with -chymotrypsin--.

Column 20, line 45, before "quantitation for the recovery", please replace "cresents" with --presents--.

UNITED STATES PATENT AND TRADEMARK OFFICE
CERTIFICATE OF CORRECTION

PATENT NO. : 5,968,957
DATED : October 19, 1999
INVENTOR(S) : Gregory S. HAMILTON et al.

It is certified that error appears in the above-indentified patent and that said Letters Patent is hereby corrected as shown below:

Column 23, line 21, before "-C6)-straight or branched", please replace "(C-1" with --(C1--.

Column 23, line 39, before "straight or branched alkenyl", please replace "O-(C2-C4)" with --O-$(C_2-C_4)$--.

Column 23, line 56, after "prevention" and before "neurodegeneration", please replace "or" with --of--.

Column 25, line 51, after "trifluoromethoxy,", please replace "(C1-C6)" with --$(C_1-C_6)$--.

Column 25, line 57, after "E is" and before "straight or branched alkyl,", please replace "(C0-$C_6$)" with --$(C_1-C_6)$--.

Column 28, line 2, after "prevention" and before "neurodegeneration", please replace "or" with --of--.

Signed and Sealed this

Twenty-seventh Day of June, 2000

Attest:

Q. TODD DICKINSON

*Attesting Officer*            *Director of Patents and Trademarks*

UNITED STATES PATENT AND TRADEMARK OFFICE
CERTIFICATE OF CORRECTION

PATENT NO. : 5,968,957
DATED : October 19, 1999
INVENTOR(S) : Gregory S. HAMILTON et al.

Page 1 of 3

It is certified that error appears in the above-indentified patent and that said Letters Patent is hereby corrected as shown below:

Column 23, line 21, before "-C6)-straight or branched", please replace "(C-1" with --(C1--.

Column 23, line 39, before "straight or branched alkenyl", please replace "O-(C2-C4)" with --O-($C_2$-$C_4$)--

Column 23, line 56, after "prevention" and before "neurodegeneration", please replace "or" with --of--.

Column 25, line 51, after "trifluoromethoxy,", please replace "(C1-C6)" with --($C_1$-$C_6$)--.

Column 25, line 57, after "E is" and before "straight or branched alkyl,", please replace "(C0-$C_6$)" with --($C_1$-$C_6$)--.

Column 28, line 2, after "prevention" and before "neurodegeneration", please replace "or" with --of--.

UNITED STATES PATENT AND TRADEMARK OFFICE
CERTIFICATE OF CORRECTION

PATENT : 5,968,957

DATED : October 19, 1999

INVENTOR(S) : Gregory S. Hamilton et al

It is certified that error appears in the above-identified patent and that said Letters Patent is hereby corrected as shown below:

Column 4, line 22, after "B and D are" and before "Ar, hydrogen, (C1-C6)-", please replace "Independently" with --independently--.

Column 14, line 40, before ". The crude residue was purified", please replace "vacua" with --vacuo--.

Column 15, line 63, before "binding protein," please replace "FKBP" with --FK506--.

Column 16, line 11, after "in a" and before "-coupled assay,", please replace "chymotropsin" with --chymotrypsin--.

Column 20, line 45, before "quantitation for the recovery", please replace "cresents' with --presents--.

UNITED STATES PATENT AND TRADEMARK OFFICE
CERTIFICATE OF CORRECTION

PATENT NO. : 5,968,957
DATED : October 19, 1999
INVENTOR(S) : Gregory S. HAMILTON It is certified that error appears in the above-indentified patent and that said Letters Patent is hereby corrected as shown below:

Column 17, Table 1, second drawing, please insert --N-- prior to "(α-toluenesulfoyl)."

Column 20, line 46, after "II" and before "quantitation," please replace "cresents" with --presents--.

Signed and Sealed this

Twenty-sixth Day of December, 2000

Attest:

Attesting Officer

Q. TODD DICKINSON
Director of Patents and Trademarks